United States Patent [19]

Hager et al.

[11] Patent Number: 5,532,399

[45] Date of Patent: Jul. 2, 1996

[54] PROCESS FOR THE PREPARATION OR ORGANOSILICON COMPOUNDS CARRYING SULFUR-CONTAINING ORGANIC RADICALS

[75] Inventors: Rudolf Hager; Josef Wolferseder, both of Altoetting; Bernward Deubzer, Burghausen, all of Germany

[73] Assignee: Wacker-Chemie GmbH, Munich, Germany

[21] Appl. No.: 190,132

[22] PCT Filed: Sep. 24, 1992

[86] PCT No.: PCT/EP92/02215

§ 371 Date: Feb. 3, 1994

§ 102(e) Date: Feb. 3, 1994

[87] PCT Pub. No.: WO93/08228

PCT Pub. Date: Apr. 29, 1993

[30] Foreign Application Priority Data

Oct. 24, 1991 [DE] Germany .......................... 41 35 170.3

[51] Int. Cl.⁶ ................................................. C07F 7/08
[52] U.S. Cl. ................................................. 556/428
[58] Field of Search ................................. 556/427, 428, 556/413, 425

[56] References Cited

U.S. PATENT DOCUMENTS 4,235,638  11/1980  Beck et al. .
4,814,471  3/1989  Renauld .
5,068,379  11/1991  Roy ........................................ 556/428

FOREIGN PATENT DOCUMENTS 742243  9/1966  Canada .
760997  6/1967  Canada .
0008902  3/1980  European Pat. Off. .
1495434  11/1969  Germany .

OTHER PUBLICATIONS

M. Litt and T. Matsuda, J. Appl. Polym. Sci. 19 (1975) 1221.

Y. Goldgerg, V. Dirnens and E. Lukevics "Journal of Organometallic Chemistry Library", vol. 20, 1988, pp. 219 to 222.

Primary Examiner—Paul F. Shaver
Attorney, Agent, or Firm—Martin Connaughton

[57] ABSTRACT

The invention relates to a process by which organosilicon compounds carrying sulfur-containing organic radicals can easily be prepared by reacting organosilicons of the general formula $$R_a(R^1O)_b R^2_c SiO_{(4-a-b-c)/2} \quad (I)$$

in which

R can be identical or different and is a monovalent organic radical, $R^1$ can be identical or different and is a hydrogen atom or a monovalent organic radical, $R^2$ can be identical or different and is a radical —QX, where Q is a divalent hydrocarbon radical and X is a halogen atom, a is 0, 1, 2 or 3, b is 0, 1, 2 or 3 and c is 0, 1, 2 or 3, with the proviso that the organosilicon compound has at least one radical $R^2$ per molecule and the sum of a, b and c is less than or equal to 4, with sulfite in the presence of water.

10 Claims, No Drawings

PROCESS FOR THE PREPARATION OR ORGANOSILICON COMPOUNDS CARRYING SULFUR-CONTAINING ORGANIC RADICALS

This application is a 371 of PCT/EP92/02215 filed Sep. 26, 1992.

The invention relates to a process for the preparation of organosilicon compounds which carry at least one radical bonded to silicon via carbon and having a sulfonate group or a grouping —SO$_2$—O— bonded to form a ring. The term sulfonate groups is to be understood hereafter as including sulfonic acid groups, SO$_3$H.

Organosilicon compounds carrying sulfonate groups are already known and can be prepared by various processes. German Offenlegungsschrift 1,495,434 (Dow Corning Corp.; published on 13th Nov. 1969) or the corresponding CA 742243 A and CA 760997 A, and U.S. Pat. No. 4,814,471 (Dow Corning Ltd.; published on 21st Mar. 1989), for example, describe processes for the preparation of organosilicon compounds containing sulfonate groups by oxidation of the corresponding thiuronium salts, thiocyano compounds and mercapto compounds with common oxidizing agents. Zwitterionic sulfonate-containing siloxanes are obtained according to M. Litt and T. Matsuda, J. Appl. Polym. Sci. 19 (1975) 1221, by the reaction of aminoalkyl-functional siloxanes with ω-alkylsultones. The sulfonation of epoxy- and alkenyl-functional organosilicon compounds with sodium hydrogensulfite is published in U.S. Pat. No. 4,235,638 (Minnesota Mining and Manufacturing Company; published on 25th Nov. 1980). Furthermore, European patent application A1-8,902 (The British Petroleum Company Ltd.; published on 19th Mar. 1980) describes a process for the modification of inorganic oxides carrying hydroxyl groups on their surface by reaction of these hydroxyl groups with trifunctional haloalkylorganyloxysilanes and subsequent treatment of these solid particles with an aqueous solution of an inorganic sulfite.

The object of the present invention was to provide a process by which organosilicon compounds carrying sulfur-containing organic radicals can easily be prepared. This object is achieved by the invention.

The present invention relates to a process for the preparation of organosilicon compounds carrying sulfur-containing organic radicals, wherein organosilicon compounds made up of units of the general formula $$R_a(R^1O)_bR^2_cSiO_{(4-a-b-c)/2} \quad (I)$$

in which

R can be identical or different and is a monovalent organic radical,

R$^1$ can be identical or different and is a hydrogen atom or a monovalent organic radical, R$^2$ can be identical or different and is a radical —QX, where Q is a divalent hydrocarbon radical and X is a halogen atom, a is 0, 1, 2 or 3, b is 0, 1, 2 or 3 and c is 0, 1, 2 or 3, with the proviso that the organosilicon compound has at least one radical R$^2$ per molecule and the sum of a, b and c is less than or equal to 4, are reacted with sulfite in the presence of water.

The organosilicon compounds obtainable by the process according to the invention contain at least one SiC-bonded group —QSO$_3$M$_v$ per molecule, in which Q is as defined above, M is a cation and v has the reciprocal value of the charge of M, or a grouping —SO$_2$—O— bonded to form a ring. Compounds having groupings —SO$_2$—O— bonded to form a ring are generally called sultones and are internal esters of compounds which carry both —SO$_3$H radicals and hydroxyl groups. (So-called "silasultones" contain the grouping

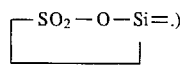

Examples of the radical M are the proton, alkali metal cations such as lithium, sodium, potassium, rubidium and cesium cations, alkaline earth metal cations such as magnesium and calcium cations, and radicals of the formula $$^+NR^3_4 \quad (V)$$

in which R$^3$ can be identical or different and is a hydrogen atom, a monovalent organic radical or an organosilicon radical, such as, for example, methyl, ethyl, n-propyl, isopropyl, n-butyl, isobutyl, n-pentyl, isopentyl, n-hexyl, benzyl, 2-hydroxyethyl and 3-hydroxypropyl radicals, as well as 3-sil(oxan)ylpropyl radicals in which the sil(oxan)yl radical can be varied at will.

The radical R is preferably a substituted or unsubstituted hydrocarbon radical having 1 to 12 carbon atoms, hydrocarbon radicals having 1 to 6 carbon atoms, especially the methyl radical, being particularly preferred.

Examples of radicals R are alkyl radicals such as the methyl, ethyl, n-propyl, isopropyl, n-butyl, isobutyl, tert-butyl, n-pentyl, isopentyl, neopentyl and tert-pentyl radicals, hexyl radicals, for example the n-hexyl radical, heptyl radicals, for example the n-heptyl radical, octyl radicals, for example the n-octyl radical, and isooctyl radicals, for example the 2,2,4-trimethylpentyl radical, nonyl radicals, for example the n-nonyl radical, decyl radicals, for example the n-decyl radical, and dodecyl radicals, for example the n-dodecyl radical; alkenyl radicals such as the vinyl and allyl radicals; cycloalkyl radicals such as the cyclopentyl, cyclohexyl, cycloheptyl and methylcyclohexyl radicals; aryl radicals such as the phenyl and naphthyl radicals; alkaryl radicals such as the o-, m- and p-tolyl, xylyl and ethylphenyl radicals; and aralkyl radicals such as the benzyl and α- and β-phenylethyl radicals.

The radical R$^1$ is preferably a hydrogen atom or a substituted or unsubstituted hydrocarbon radical having 1 to 6 carbon atoms, the hydrogen atom and alkyl radicals having 1 to 3 carbon atoms, especially the methyl, ethyl and isopropyl radicals, being particularly preferred.

Examples of radicals R$^1$ are the examples having 1 to 6 carbon atoms mentioned for the radical R.

The radical Q is preferably a divalent hydrocarbon radical having 2 to 10 carbon atoms.

Examples of the radical Q are the ethylene, n-propylene, isopropylene, 1-n-butylene, 2-n-butylene, isobutylene, tert-butylene, n-pentylene, isopentylene, neopentylene and tert-pentylene radicals, hexylene radicals, for example the n-hexylene radical, heptylene radicals, for example the n-heptylene radical, octylene radicals, for example the n-octylene radical, and isooctylene radicals, for example the 2,2,4-trimethylpentylene radical, nonylene radicals, for example the n-nonylene radical, and decylene radicals, for example the n-decylene radical, as well as cycloalkylene radicals such as the cyclopentylene, cyclohexylene, cycloheptylene and methylcyclohexylene radicals.

Q is particularly preferably the n-propylene radical.

The halogen atom X is for example chlorine, bromine or iodine, X preferably being a chlorine atom.

The radicals $R^2$ are preferably —$(CH_2)_3Cl$, $(CH_2)_3Br$, —$(CH_2)_4Cl$, —$(CH_2)_4Br$, —$(CH_2)_2CH(CH_3)Cl$ or —$(CH_2)_5Cl$, —$(CH_2)_3Cl$ being particularly preferred.

The organosilicon compounds made up of units of formula (I) and used in the process according to the invention are preferably silanes of the general formula $$R^6_d(R^7O)_eSiR^8_g \qquad (II)$$

and/or partial hydrolyzates thereof, in which $R^6$ can be identical or different and is as defined above for R, $R^7$ can be identical or different and is as defined above for $R^1$, $R^8$ can be identical or different and is as defined above for $R^2$, d is 0, 1, 2 or 3, preferably 0, 1 or 2 and particularly preferably 1 or 2, e is 0, 1, 2 or 3, preferably 1, 2 or 3 and particularly preferably 1 or 2, and g is 1, 2 or 3, preferably 1 or 2 and particularly preferably 1, with the proviso that the sum d+e+g is equal to 4.

Examples of silanes of formula (II) which can be used in the process according to the invention are $(CH_3)_3Si(CH_2)_3Cl$, $C_6H_5(CH_3)_2Si(CH_2)_3Br$, $(CH_3)_2(OH)Si(CH_2)_3Cl$, $(CH_3)_2(CH_3O)Si(CH_2)_3Cl$, $(CH_3)_2(C_2H_5O)Si(CH_2)_3Cl$, $(C_2H_5)_2(CH_3O)Si(CH_2)_4Cl$, $CH_3(CH_3O)_2Si(CH_2)_3Cl$,

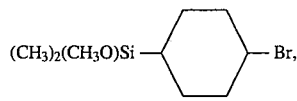

$CH_3(C_2H_5O)_2Si(CH_2)_3$, $CH_2{=}CH(CH_3O)_2Si(CH_2)_4Cl$, $CH_3(C_3H_7O)_2Si(CH_2)_2CH(CH_3)Br$, $(CH_3O)_3Si(CH_2)_3Cl$, $(CH_2H_5O)_3Si(CH_2)_4$, $CH_3(CH_3O)Si[(CH_2)_3Cl]_2$, $(CH_3O)_2Si[(CH_2)_3Cl]_2$, $(CH_3O)_2Si[(CH_2)_4Br]_2$, $CH_3Si[(CH_2)_3I]_3$ and $(CH_3O)Si[(CH_2)_3I]_3$, $(CH_3)_2(HO)Si(CH_2)_3Cl$, $(CH_3)_2(CH_3O)Si(CH_2)_3Cl$, $(CH_3)_2(C_2H_5O)Si(CH_2)_3Cl$, $CH_3(CH_3O)Si[(CH_2)_3Cl]_2$, $CH_3(CH_3O)_2Si(CH_2)_3Cl$, $CH_3(C_2H_5O)_2Si(CH_2)_3Cl$, $C_6H_5(CH_3O)_2Si(CH_2)_3Cl$, $C_6H_5(C_2H_5O)_2Si(CH_2)_3Cl$, $(C_2H_5O)_3Si(CH_2)_3Cl$ and $(CH_3O)_2Si(CH_2)_3Cl$ being preferred and $(CH_3)_2(CH_3O)Si(CH_2)_3Cl$, $(CH_3)_2(C_2H_5O)Si(CH_2)_3Cl$, $(CH_3)(CH_3O)_2Si(CH_2)_3Cl$ and $(CH_3)(C_2H_5O)_2Si(CH_2)_3Cl$ being particularly preferred.

However, the organosilicon compounds made up of units of formula (I) and used in the process according to the invention can also be organo(poly)siloxanes if the sum a+b+c in the units of formula (I) is less than or equal to 3.

If the organosilicon compound made up of units of formula (I) and used according to the invention is an organo(poly)siloxane, a has an average value preferably of 0.5 to 2.5 and particularly preferably of 0.9 to 2.1, b has an average value preferably of 0 to 0.5 and particularly preferably of 0 to 0.3, and c has an average value preferably of 0.1 to 1.5 and particularly preferably of 0.3 to 1.0.

Examples of organo(poly)siloxanes which can be used in the process according to the invention are linear organo(poly)siloxanes such as $O[Me_2Si(CH_2)_3Cl]_2$, $Me[Me_3SiO]_2Si(CH_2)_3Cl$, $Cl(CH_2)_3SiMe_2O[SiMe_2O]_5Me_2Si(CH_2)_3Cl$, $HOMe_2SiO[SiMe_2O]_{10}[MeSi((CH_2)_3Cl)O]_5Me_2SiOH$, $Me_3SiO[SiMe_2O]_7[MeSi((CH_2)_3Cl)O]_2SiMe_3$, $O[Me_2Si(CH_2)_4Cl]_2$ and $Me_3SiOSiMe_2(CH_2)_3Cl$, cyclic organo(poly)siloxanes such as $[OMeSi(CH_2)_3Cl]_{3-8}$, $[OMeSi(CH_2)_4Br]_{3-8}$, $[OMeSi(CH_2)_3Cl]_2[OMe_2Si]_2$ and $[O(C_2H_5)Si(CH_2)_4Br]_2[OMe_2Si]_3$, and branched organo(poly)siloxanes such as $[Me_3SiO]_3Si(CH_2)_3Cl$ and $<[Me_3SiO]_2Si(CH_2)_3Cl>_2O$, $O[Me_2Si(CH_2)_3Cl]_2$, $HOMe_2SiO[SiMe_2O]_{10}[MeSi((CH_2)_3Cl)O]_5Me_2SiOH$ and $[Me_3SiO]_2MeSi(CH_2)_3Cl$ being preferred and $O[Me_2Si(CH_2)_3Cl]_2$ being particularly preferred, Me being the methyl radical.

Silanes of the general formula $$R^4_fSi(OR^5)_{4-f} \qquad (III)$$

and/or partial hydrolyzates thereof, in which $R^4$ can be identical or different and is as defined for R, $R^5$ can be identical or different and is as defined for $R^1$, and f is 0, 1, 2 or 3, preferably 1, 2 or 3 and particularly preferably 2 or 3, can also be used in the process according to the invention.

A silane of formula (III) and/or a partial hydrolyzate thereof is used especially together with an organosilicon compound made up of units of formula (I) which carries at least one radical $R^1$ per molecule.

In a preferred embodiment of the process according to the invention, at least one silane of the general formula $$R^6_d(R^7O)_eSiR^8_g \qquad (II)$$

and/or a partial hydrolyzate thereof, in which $R^6$, $R^7$, $R^8$, d, e and g are as defined above, with the proviso that the sum d+e+g is equal to 4 and e is an integer other than 0, and, if appropriate, at least one silane of the general formula $$R^4_fSi(OR^5)_{4-f} \qquad (III)$$

and/or a partial hydrolyzate thereof, in which $R^4$, $R^5$ and f are as defined above, is reacted with sulfite in the presence of water.

If a silane of formula (III) is used in the process according to the invention, it is used in amounts preferably of 5 to 1200 percent by weight and particularly preferably of 20 to 500 percent by weight, based in each case on the total weight of organosilicon compound made up of units of formula (I).

Organosilicon compounds made up of units of formula (I) are commercially available compounds or can be prepared by methods commonly employed in silicon chemistry. Thus, for example, chloroalkyl-functional organosilicon compounds can be prepared by the platinum-catalyzed hydrosilylation of allyl chloride with the appropriate hydridofunctional organosilicon compounds. Bromo- and iodofunctional organosilicon compounds are accessible by an analogous method, but are preferably obtained from the corresponding chloro compounds by exchange of the halogen atom. A reaction procedure involving phase transfer catalysis is found to be advantageous here, such a procedure being described for silanes by Y. Goldberg, V. Dirnens and E. Lukevics in "Journal of Organometallic Chemistry Library", vol. 20, 1988, pages 219 to 222.

The sulfite used in the process according to the invention is preferably a compound which is soluble in water at 100° C. and 1013 hPa to the extent of at least 20 percent by weight, based on the total weight of the solution, said compound having the formula $$(M'_{v'})_2SO_3 \qquad (IV)$$

in which M' can be identical or different and is as defined above for M, with the exception of the proton, and v' has the reciprocal value of the charge of M'.

Examples of M' are the examples given above for M, with the exception of the proton.

The radical M' is preferably the sodium ion, potassium ion or ammonium ion, M' particularly preferably being the sodium ion.

Examples of sulfites used in the process according to the invention are $Na_2SO_3$, $(NH_4)_2SO_3$, $K_2SO_3$, $(NMe_4)_2SO_3$, $(NEt_3Benz)_2SO_3$, $(NMe_3H)_2SO_3$ and $(NEtH_3)_2SO_3$, $Na_2SO_3$, $K_2SO_3$ and $(NH_4)_2SO_3$ being preferred and $Na_2SO_3$ being particularly preferred, Me being the methyl radical, Et the ethyl radical and Benz the benzyl radical.

In the process according to the invention, sulfite is used in amounts preferably of 0.8 mol to 1.5 mol, particularly preferably of 0.9 mol to 1.1 mol and especially of 1 mol, based in each case on one mol of radical X in the organosilicon compound made up of units of formula (I) and used according to the invention. One mol of sulfite per mol of radical X in the organosilicon compound made up of units of formula (I) and used according to the invention is generally totally sufficient to achieve a homogeneous reaction mixture and a complete conversion of the radicals X. However, a complete conversion of the radicals X is achieved more rapidly with an excess of sulfite.

In the process according to the invention, water is used in amounts preferably of 50 to 1000 percent by weight and particularly preferably of 200 to 700 percent by weight, based in each case on the weight of organosilicon compound made up of units of formula (I).

Furthermore, a water-soluble organic solvent can additionally be used in the process according to the invention, in amounts preferably of 0 to 1000 percent by weight and particularly preferably of 0 to 500 percent by weight, based in each case on the weight of water used.

Examples of water-soluble organic solvents are methanol, ethanol, isopropanol, ethylene glycol, ethylene glycol dimethyl ether, diethylene glycol dimethyl ether, tetrahydrofuran, 1,4-dioxane, N,N-dimethylformamide, dimethyl sulfoxide or sulfolan, as well as mixtures thereof, methanol, ethanol and isopropanol being preferred and ethanol being particularly preferred.

The reaction according to the invention can be accelerated by using a catalyst in the process according to the invention. A catalyst is preferably used in the process according to the invention when a silane of formula (II) in which e is equal to 0, or an organo(poly)siloxane having predominantly apolar organic radicals, is used as the organosilicon compound made up of units of formula (I).

Examples of catalysts which can be used in the process according to the invention are phase transfer catalysts such as, for example, quaternary ammonium or phosphonium compounds, crown ethers or linear polyethylene glycol diethers: $NBu_4^+Cl^-$, $NBu_4^+Br^-$, $NBu_4^+HSO_4^-$, $NBu_4^+OAc^-$, $Et_3BenzN^+Cl^-$, $Oct_3MeN^+Cl^-$, $Bu_3BenzN^+$ $Cl^-$, $C_{16}H_{33}NMe_3^+Cl^-$, $Ph_3EtP^+Cl^-$, $Ph_3BenzP^+Br^-$, $Bu_4P^+Cl^-$, [18]-crown-6, dibenzo-[18]-crown-6, dicyclohexyl-[18]-crown- 6 and $CH_3(OCH_2CH_2)_xOCH_3$ (e.g. x=5, 11, 22), $NBu_4^+Cl^-$, $NBu_4^+Br^-$, $NBu_4^{+HSO_4^-}$, $NBu_4^+OAc^-$, $Oct_3MeN^+Cl$, [18]-crown-6 and dibenzo-[18]-crown-6 being preferred and $NBu_4^+Cl^-$, $NBu_4^+HSO_4^-$ and $Oct_3MeN^+Cl^-$ being particularly preferred, Me being the methyl radical, Bu the butyl radical, Ph the phenyl radical, Benz the benzyl radical and Oct the octyl radical.

If a catalyst is used in the process according to the invention, it can be used in any desired amounts, but preferably of 0.1 to 10 mol percent and particularly preferably of 1 to 5 mol percent, based in each case on the radical X in the organosilicon compound made up of units of formula (I) and used according to the invention.

The individual constituents used in the process according to the invention can be in each case one type of such constituents or a mixture of at least two types of such constituents.

The process according to the invention is carried out at a temperature preferably of 20° C. to 220° C. and particularly preferably of 50° to 180° C., and at a pressure preferably of between 900 and 50,000 hPa and particularly preferably of between 900 and 20,000 hPa. However, the process according to the invention can also be carried out at higher or lower pressures.

In the process according to the invention, the individual constituents used according to the invention can be mixed together in any desired order.

In the process according to the invention, when using an organosilicon compound made up of units of formula (I) which carries hydrolyzable groups such as, for example, organyloxy groups, or when using a silane of formula (III) and/or a partial hydrolyzate thereof, the hydrolyzable organosilicon compound is preferably metered slowly, after the desired reaction conditions have been established, into a mixture of the other constituents used according to the invention.

When the process according to the invention has ended, the resulting organosilicon compounds carrying sulfur-containing organic radicals can be isolated by any of the processes which have also been applied hitherto for the isolation of organosilicon compounds carrying sulfur-containing organic radicals. When the process according to the invention has ended, however, the resulting organosilicon compounds carrying sulfur-containing organic radicals can also be subjected to further reactions directly. Various methods of isolation can be applied, depending on the composition of the compounds. If, for example, the organosilicon compounds made up of units of formula (I) which are used in the process according to the invention are exclusively silanes of formula (II) or organo(poly)siloxanes containing at least one radical $R^2$ on each silicon atom, $R^2$ being as defined above, the products are preferably isolated by a procedure in which, after evaporation, the reaction mixtures are treated with acids, preferably 37% hydrochloric acid, mixed with water-soluble organic solvents, especially ethanol or isopropanol, preferably in amounts of 100 to 400 percent by weight, based on the weight of the concentrated acid, whereupon the organosilicon compounds carrying sulfur-containing organic radicals pass into solution as sulfonic acids, while the salts obtained as by-products, such as, for example, M'Cl, where M' is as defined above, remain undissolved and can thus be filtered off. Sulfite which may have been used in excess gives sulfurous acid in the acid treatment, which decomposes with the release of $SO_2$ when the product-containing solution is evaporated, preferably at 50° to 100° C. and 5 to 50 Pa. A variant of the working-up method described is possible when the reaction according to the invention is carried out with the preferred $Na_2SO_3$: In this case, the reaction mixture is saturated with gaseous hydrogen chloride without prior evaporation, NaCl precipitating out quantitatively on cooling to 0° C. After filtration, the product-containing solution is evaporated analogously to the procedure described above. The resulting products are silanes, organo(poly)siloxanes or so-called "silasultones" carrying sulfonic acid groups. Said silasultones can be isolated in particular by evaporating reaction mixtures obtained by the reaction of organosiloxanes made up of units of formula (I) in which a=2, b=0 and c=1, or of organosilanes of formula (II) in which d=2, e=1 and g=1.

If organo(poly)siloxanes made up of units of formula (I) in which the average value c is well below 1, or a mixture of silanes of formulae (II) and (III), are reacted with sulfite by the process according to the invention, the organosilicon compound carrying sulfur-containing organic radicals is preferably isolated by a procedure in which the reaction mixture is evaporated when the reaction has ended, and the products are separated from the resulting residue by extraction with an organic solvent. The polarity of the organic solvent depends on the number of sulfonate groups in the organosilicon compound. Alcohols such as ethanol or isopropanol are preferred.

Organosilicon compounds carrying sulfur-containing organic radicals and obtained by the process according to the invention can also be modified before isolation. If, for example, the product mixture contains organo(poly)siloxanes carrying a C-bonded sulfonate group on each Si atom, these can very easily be modified by reaction of this product mixture with silanes of formula (III). The resulting products can then be isolated by extraction as described above, making an acid treatment superfluous.

The cation of the organosilicon compound obtained in the process according to the invention, which carries at least one organic radical having a sulfonate group—$SO_3M_v$, where M and v are as defined above, can easily be varied at will. For example, in the case where M is a metal cation or a radical of formula (V), the organosilicon compound prepared according to the invention can be treated with an acid such as, for example, sulfuric acid or hydrochloric acid, or with an acidic ion exchanger, to give organosilicon compounds having —$SO_3H$ groupings, or the cations M can be replaced with any other cations using an ion exchanger. If M is a proton in the organosilicon compound prepared according to the invention, it can be neutralized with a base to give organosilicon compounds carrying a group $SO_3M''$, where M" is as defined for M'.

The process according to the invention has the advantage that organosilicon compounds which contain at least one radical bonded to silicon via carbon and having a sulfonate group or a grouping —$SO_2$—O— bonded to form a ring are easy to prepare. The process according to the invention has the further advantage of using toxicologically acceptable, readily available and inexpensive starting compounds. Thus organosilicon compounds carrying chlorine-substituted organic radicals can preferably be used in the process according to the invention without having to accept low reaction rates.

Further advantages of the process according to the invention are the high yields of organosilicon compounds carrying sulfur-containing organic radicals, which are over 90%. Another advantage is the fact that relatively simple working-up and isolation methods can be chosen in the process according to the invention.

The consistency of the organosilicon compounds carrying sulfur-containing organic radicals and prepared by the process according to the invention ranges from liquid to solid, depending on the type of organosilicon compound used and on the type of cation in the case of sulfonate groups. If silanes of formula (II) in which e is equal to 0 are used in the process according to the invention as organosilicon compounds made up of units of formula (I), silanes carrying sulfonate groups are obtained. If silanes of formula (II) in which e is other than 0 are used in the process according to the invention as organosilicon compounds made up of units of formula (I), organo(poly)siloxanes are obtained which carry on each Si atom an organic radical containing a sulfonate group, or, depending on the conditions, have a grouping —$SO_2$—O— bonded to form a ring. If silanes of formula (II) in which e is other than 0 and silanes of formula (III) and/or partial hydrolysates thereof are used in the process according to the invention as organosilicon compounds made up of units of formula (I), organo(poly)siloxanes are obtained which are composed of different siloxane units, depending on the type of the individual silanes and the amounts used. Corresponding organo(poly)siloxanes are obtained when the product mixture of the reaction according to the invention of silanes of formula (II) in which e is other than 0 is reacted with silanes of formula (III) and/or partial hydrolyzates thereof after the nucleophilic substitution but before the working-up.

If the proportion of polar radicals in the organosilicon compounds prepared by the process according to the invention is sufficiently high, said compounds are water-soluble.

If desired, the organosilicon compounds obtained by the process according to the invention which carry at least one radical bonded to silicon via carbon and having a sulfonate group or a grouping —$SO_2$—O— bonded to form a ring can be equilibrated with at least one organo(poly)siloxane (1). The equilibration can be carried out by processes conventionally employed in silicon chemistry.

Organo(poly)siloxanes (1) with which the organosilicon compound prepared according to the invention is equilibrated, if desired, are preferably those made up of units of the general formula $$R^9_i(R^{10}O)_h SiO_{(4-i-h)/2} \qquad (VI)$$

in which $R^9$ can be identical or different and is a hydrogen atom or a monovalent organic radical, $R^{10}$ can be identical or different and is as defined for $R^1$, i is 0, 1, 2 or 3 and h is 0, 1, 2 or 3, with the proviso that the sum of i and h is less than or equal to 3.

Examples of organopolysilicon compounds (1) are linear organo(poly)siloxanes carrying terminal triorganosiloxy groups and having 2 to 200 silicon units, linear organo(poly)siloxanes carrying terminal hydroxyl groups and having 2 to 200 silicon units, and cyclic organo(poly)siloxanes having 3 to 12 silicon units.

If the organosilicon compound according to the invention, carrying sulfur-containing organic radicals, is equilibrated with organo(poly)siloxanes (1) carrying at least one organic radical having an amino functional group, organosilicon compounds are obtained which contain both an organic radical having an —$SO_3^-$ grouping and an amino-functional organic radical per molecule and thus have a zwitterionic structure.

Examples of amino-functional organo(poly)siloxanes (1) with which the organosilicon compounds according to the invention can be equilibrated, if desired, are

     where A = —$(CH_2)_3NH_2$ and X = 0 to 20,

-continued

A—SiMe$_2$—[OSiMe$_2$]$_x$OSiMe$_2$—A  where A = —(CH$_2$)$_3$NH(CH$_2$)$_2$NH$_2$ and x = 0 to 20, Me$_3$Si[OSiMe$_2$]$_y$[OSiMe]$_z$OSiMe$_3$
               |
               A
where A = —(CH$_2$)$_3$NH$_2$, y = 0 to 20 and z = 1 to 15, Me$_3$Si[OSiMe$_2$]$_y$[OSiMe]$_z$OSiMe$_3$
               |
               A
where A = —(CH$_2$)$_3$NH(CH$_2$)$_2$NH$_2$, y = 0 to 20 and z = 1 to 15, H[OSiMe$_2$]$_y$[OSiMe]$_z$OH
         |
         A
where A = —(CH$_2$)$_3$NH$_2$, y = 0 to 20 and z = 2 to 20, H[OSiMe$_2$]$_y$[OSiMe]$_z$OH
         |
         A
where A = —(CH$_2$)$_3$NH(CH$_2$)$_2$NH$_2$, y = 0 to 20 and z = 2 to 20,

[OSiMe]$_k$
  |
  A
where A = —(CH$_2$)$_3$NH$_2$ and k = 3 to 12, and

[OSiMe]$_k$
  |
  A
where A = —(CH$_2$)$_3$NH(CH$_2$)$_2$NH$_2$ and k = 3 to 12, Me being the methyl radical.

The amount and type of the organopolysilicon compound (1) used in the optional equilibration step of the process according to the invention are determined only by the desired proportion of sulfur-containing organic radicals in the organosilicon compound produced in the optional equilibration step of the process according to the invention, and by the desired average chain length.

If the organosilicon compound to be equilibrated, produced by the process according to the invention, contains free sulfonic acid groups or so-called silasultone groupings, which spontaneously form sulfonic acid groups on the addition of water, said groups themselves promote the equilibration, so no additional equilibration catalyst is required in this case. This is a preferred procedure.

In the case of organosilicon compounds having neutralized sulfonic acid groups, the optional equilibration is preferably carried out in the presence of catalysts which promote the equilibration. Examples of such catalysts are basic catalysts such as, for example, alkali metal hydroxides like sodium hydroxide and potassium hydroxide, trimethylbenzylammonium hydroxide, tetramethylammonium hydroxide and potassium trimethylsilanolate, and acid catalysts such as, for example, sulfuric acid, phosphoric acid, trifluoromethanesulfonic acid, phosphorus nitridochlorides and acid catalysts which are solid under the reaction conditions, such as acid-activated bleaching earth, acid zeolites, sulfonated charcoal and sulfonated styrene/divinylbenzene copolymer, basic catalysts generally being preferred.

If an equilibration catalyst is employed, it is used in amounts preferably of 0.005 to 0.5 percent by weight and especially of 0.02 to 0.1 percent by weight, based in each case on the total weight of the organosilicon compounds used.

The optional equilibration is preferably carried out at 80° C. to 150° C. and at the pressure of the surrounding atmosphere, i.e. between 900 and 1100 hPa. If desired, however, higher or lower pressures can also be applied.

Furthermore, if they carry organyloxy groups or hydroxyl groups, the organosilicon compounds prepared by the process according to the invention can be subjected to hydrolysis or condensation. The hydrolysis and condensation of organosilicon compounds having organyloxy groups or hydroxyl groups are already known in many instances. For example, the organosilicon compounds according to the invention can be reacted with linear or cyclic organosilicon compounds carrying hydroxyl groups, such as, for example, α,ω-dihydroxydimethyl(poly)siloxane, in the presence of a catalyst such as, for example, organotin compounds, titanium and zirconium esters, quaternary nitrogen bases and mineral acids, and, if appropriate, in the presence of a solvent, hydrolysis and condensation being carried out preferably at between 23° and 150° C. and particularly preferably at between 60° and 120° C. and at a pressure of between 900 and 1100 hPa Organosilicon compounds having cyclic groupings

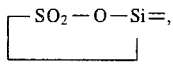

prepared by the process according to the invention, can be reacted with organosilanes or organo(poly)siloxanes (1) carrying Si-bonded hydroxyl groups, even without a catalyst, to give, with ring opening, organosilicon compounds containing sulfonate groups. Thus, for example, the reaction of α-hydroxy-ω-trimethylsilyldimethyl(poly)siloxane with 4,4-dimethyl-4-silabutane-1,4-sultone readily gives organosilicon compounds which selectively contain organic radicals carrying sulfonate groups at only one end of the chain.

The process according to the invention can be carried out batchwise, semicontinuously or fully continuously.

The organosilicon compounds carrying sulfonate groups, prepared according to the invention, have a broad spectrum of application. They can be used for all the purposes for which organosilicon compounds carrying sulfonate groups have also been used hitherto. Because the organosilicon compounds carrying sulfonate groups, prepared according to the invention, preferably carry both hydrophilic and hydrophobic groups, these compounds exhibit strong surfactant properties. They are therefore outstandingly suitable as emulsifiers and for reducing the surface tension in aqueous media, so they can act either as foam-forming agents or as antifoams, depending on their composition and the medium in which they are used.

Metallic surfaces which are in constant contact with corrosive aqueous solutions can be protected from corrosion by treatment with organosilicon compounds carrying sulfonate groups.

Glass and ceramic surfaces can be rendered permanently hydrophilic with sulfonate-functional organosilicon compounds, the silasultones or organo(poly)siloxanes having silasultone groupings which can be prepared by the process according to the invention being particularly suitable because of their high reactivity towards nucleophiles.

In the Examples described below, all viscosity data relate to a temperature of 25° C. Unless indicated otherwise, the following Examples are carried out at the pressure of the surrounding atmosphere, i.e. at about 1000 hPa, and at room temperature, i.e. at about 23° C., or at the temperature which is established when the reactants are brought together at room temperature without additional heating or cooling. Also, unless indicated otherwise, all parts and percentages are by weight.

The following abbreviations are used:

Me: methyl radical

Et: ethyl radical

EXAMPLE 1

A mixture of 40 g of 1,3-bis(3-chloropropyl)tetramethyldisiloxane (0.139 mol) and a solution of 39 g of sodium sulfite and 2.4 g of tetrabutylammonium hydrogen sulfate in 200 ml of water is heated to 180° C. in an autoclave (internal volume 750 ml), a pressure of approx. 1.3 MPa being established, and is stirred at this temperature for 20 hours. It is then cooled to room temperature—the pressure inside the autoclave now corresponds approximately to the surrounding atmospheric pressure again—and the autoclave is emptied. The homogeneous clear reaction mixture is concentrated to dryness at 60° C. and 50 Pa. The resulting white solid is treated at 0° C. with 35 ml of concentrated hydrochloric acid (37% in water) and 75 ml of isopropanol, the sodium chloride which has precipitated out is filtered off and the filtrate is freed from the volatile constituents at 60° C. and 10 Pa. With the careful exclusion of moisture, the oily residue is heated to 80° C. with 100 ml of anhydrous toluene, the solution is then filtered and the solvent is removed under reduced pressure (60° C., 30 Pa) Within a few hours at room temperature, the residue crystallizes to a yellowish brown solid, which can be identified unambiguously as the cyclic silane of the formula

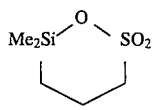

by NMR spectroscopy. By vacuum distillation (30 Pa), 46.7 g (93% of theory) of highly pure 4,4-dimethyl-4 -silabutane-1,4-sultone are obtained as a colorless solid at a still temperature of approx. 125° C.; it melts at 63° C. and its melt boils at 105° C. under a pressure of 20 Pa. The compound is hygroscopic and rapidly hydrolyzes in moist air to

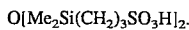

EXAMPLE 2

10 g of 3-chloropropyldimethylmethoxysilane (0.060 mol) are metered continuously, over 2 hours, into a boiling solution of 8.3 g of sodium sulfite in 50 ml of water, with intensive stirring. The mixture is then stirred for a further 12 hours under reflux. After cooling to room temperature, the slightly turbid solution is treated with 20 ml of diethyl ether and the clear aqueous phase is separated off and evaporated under a water-jet vacuum. The residual white solid is taken up at 0° C. in 15 ml of concentrated hydrochloric acid (37% in water) and 20 ml of ethanol and the solution is filtered and evaporated under an oil-pump vacuum (20 Pa) at 65° C. The resulting light yellow oil crystallizes on cooling to room temperature. With a melting point of 63° C. and a boiling point of 106° C. at 20 Pa, the substance is 4,4 -dimethyl-4-silabutane-1,4-sultone as in Example 1. The yield is 10.2 g, or 94% based on the silane used.

EXAMPLE 3

A solution of 25 g of 4,4-dimethyl-4-silabutane-1,4-sultone from Example 1 and 50 g of the siloxane of the formula HO[Me$_2$SiO]$_{15}$H in a mixture of 50 ml of ethylene glycol dimethyl ether and 2.5 ml of water is stirred at 80° C. for 4.5 hours. After cooling to room temperature, 30 g of triethylamine are metered in over 15 minutes, with stirring. To eliminate or lighten the orange-brown coloration which appears when the amine is added, the reaction mixture is stirred for a further 2 hours with 5 g of activated charcoal at room temperature and the activated charcoal is then filtered off. After removal of the volatile constituents at 55° C. under vacuum (20 Pa), 85.8 g of a clear, pale yellow oil with a viscosity of 1550 mm$^2$s$^{-1}$ are obtained, the composition of which corresponds to the formula

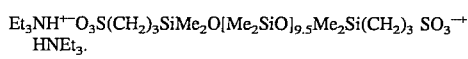

Due to the dissociation of the ammonium sulfonate groups, an aqueous solution of the substance gives an acid reaction (pH 4 for a 1% solution). Decomposition consequently takes place, as recognized by the initially clear solution slowly becoming turbid. The decomposition can be avoided if the pH of the solution is adjusted to 7 to 10 by the addition of a base (NEt$_3$, Na$_2$CO$_3$, NaOH etc.). A one percent aqueous solution neutralized with triethylamine has a surface tension of 3.4.10$^{-2}$ Nm$^{-1}$.

EXAMPLE 4

Analogously to the procedure described in Example 3, 115.5 g of a slightly yellowish oil (ν=1430 mm$^2$s$^{-1}$) of the formula

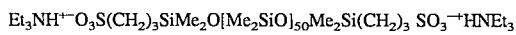

are obtained starting from a solution of 10 g of 4,4 -dimethyl-4-silabutane-1,4-sultone from Example 1 and 107 g of a polysiloxane of average composition HO[Me$_2$SiO]$_{15}$H in 100 ml of ethylene glycol dimethyl ether with which 1 ml of water is mixed, after neutralization of the initially formed sulfonic acid groups with 8 g of triethylamine.

EXAMPLE 5

100 g of 3-chloropropyldimethoxymethylsilane (0.547 mol) are metered continuously, over 8 hours, into a boiling solution of 75.9 g of sodium sulfite in 500 ml of water, with vigorous stirring. The mixture is then stirred for a further 2 hours under reflux. On cooling to room temperature, a thin organic phase, consisting mainly of poly(3-chloropropylmethyl)siloxanes with terminal methoxy groups, separates out on the water. This water-immiscible layer (3.1 g) is separated off in a separating funnel and the aqueous phase is concentrated to half its original volume at 65° C. under a water-jet vacuum. HCl gas is then passed into the aqueous solution at 0° C. until saturation is reached, the salt which has precipitated out is filtered off and the filtrate is first concentrated under a water-jet vacuum and then heated at 80° C. and at a pressure of 10 Pa. Approx. 98% of the resulting clear, almost colorless, highly viscous residue consists of units of the formula OSiMe(CH$_2$)$_3$SO$_3$H.

Yield: 89.5 g (89.7% based on silane used).

EXAMPLE 6

A dispersion of 100 g of 3-chloropropyldiethoxymethylsilane (0.474 mol) and 65.8 g of sodium sulfite in a mixture of 500 ml of water and 100 ml of ethanol is refluxed for 22 hours, with vigorous stirring. After the reaction mixture has cooled to room temperature, two phases separate out. The specifically less dense phase (14.3 g) consists predominantly of poly(3-chloropropylmethyl)siloxanes with terminal ethoxy groups, and ethanol. The aqueous phase is evaporated under a water-jet vacuum. The residual white solid is dispersed in a mixture of 100 ml of 37% hydrochloric acid in water and 150 ml of ethanol and this dispersion is cooled to 0° C. and filtered. The filtrate is first concentrated under a water-jet vacuum and then heated at 65° C. under an oil-pump vacuum (10 Pa). The resulting highly viscous, honey-like product is a polysiloxane composed of almost 97% of units of the formula OSiMe(CH$_2$)$_3$SO$_3$H and about 3% of units of the formula OSiMe(CH$_2$)$_3$Cl.

Yield: 71.6 g (83.4% based on silane used).

EXAMPLE 7

8.13 g of octamethylcyclotetrasiloxane, 1.24 g of hexamethyldisiloxane and 5 g of poly(3-sulfonylpropylmethyl)siloxane from Example 5 are dissolved in 15 ml of ethylene glycol dimethyl ether and stirred for 5 hours at 80° C. The reaction mixture is then cooled to 50° C. and treated with 3.5 g of triethylamine. After removal of the volatile constituents at 50° C. and at a pressure of 30 Pa, 16.1 g of a light yellow oil of average composition

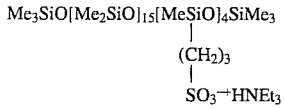

Me$_3$SiO[Me$_2$SiO]$_{15}$[MeSiO]$_4$SiMe$_3$
|
(CH$_2$)$_3$
|
SO$_3$⁻⁺HNEt$_3$ are obtained. The substance is water-soluble, but the solution becomes turbid within a few hours. The reason for this is the dissociation of the ammonium sulfonate groups, whose acid reaction initiates decomposition reactions. The aqueous solution remains stable if the dissociation of the ammonium sulfonate groups is suppressed by the addition of a base and the pH is adjusted to between 7 and 10. Turbidity again occurs in the strongly alkaline region (pH>10).

EXAMPLE 8

The equilibration reaction described in Example 7 is repeated, except that the neutralization is carried out with 10 g of 29% aqueous sodium carbonate solution in place of the triethylamine. After the volatile constituents have been stripped off, 14 g of a white solid of the formula

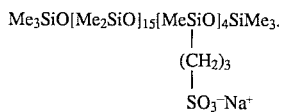

Me$_3$SiO[Me$_2$SiO]$_{15}$[MeSiO]$_4$SiMe$_3$.
|
(CH$_2$)$_3$
|
SO$_3$⁻Na⁺ are obtained. An aqueous solution of the compound gives a neutral reaction and remains consistently clear, even over a prolonged period.

EXAMPLE 9

The equilibration reaction described in Example 7 is repeated, except that the neutralization of the sulfonic acid groups is carried out using 13.3 g of an amino-functional polydimethylsiloxane of average composition H$_2$N(CH$_2$)$_3$Me$_2$SiO[Me$_2$SiO]$_{10}$SiMe$_2$(CH$_2$)$_3$NH$_2$ (0.013 mol) in place of the triethylamine. After removal of the solvent and other volatile components at 50° C. and 30 Pa, 26.6 g of a light yellow, highly viscous oil of the formula

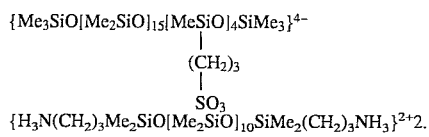

{Me$_3$SiO[Me$_2$SiO]$_{15}$[MeSiO]$_4$SiMe$_3$}$^{4-}$
|
(CH$_2$)$_3$
|
SO$_3$
{H$_3$N(CH$_2$)$_3$Me$_2$SiO[Me$_2$SiO]$_{10}$SiMe$_2$(CH$_2$)$_3$NH$_3$}$^{2+}$2.

remain.

EXAMPLE 10

A solution of 5.3 g of poly(3-sulfonylpropylmethyl)siloxane, prepared according to Example 5, 13.4 g of octamethylcyclotetrasiloxane and 0.71 g of 1,3-divinyl-1,1,3,3-tetramethyldisiloxane in 15 ml of ethylene glycol dimethyl ether is stirred for 10 hours at 80° C. After cooling to room temperature, 29.6 g of a 25% solution of tetrabutylammonium hydroxide in methanol are added. The solvents and volatile compounds are removed at 60° C. and 20 Pa. 24.5 g of a light yellow, pulpy, water-soluble mass of average composition

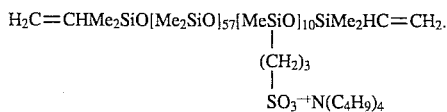

H$_2$C=CHMe$_2$SiO[Me$_2$SiO]$_{57}$[MeSiO]$_{10}$SiMe$_2$HC=CH$_2$.
|
(CH$_2$)$_3$
|
SO$_3$⁻⁺N(C$_4$H$_9$)$_4$ remain.

EXAMPLE 11

20 g of poly(3-sulfonylpropylmethyl)siloxane, synthesized by the process described in Example 5, and 90 g of hexamethyldisiloxane are dissolved at 80° C. in 200 ml of ethylene glycol dimethyl ether and stirred at this temperature for 15 hours. The reaction mixture is then cooled to room temperature and divided up into equal volumes in two vessels. The contents of one vessel are treated with 7 g of triethylamine, with stirring, and ammonia gas is passed into the solution in the other vessel until it gives a distinct alkaline reaction. Both solutions are then evaporated at 50° C. and at a pressure of 20 Pa. The resulting products (23.7 g of a light yellow oil in the case of neutralization with NEt$_3$, 18.4 g of an orange pasty substance in the case of neutralization with NH$_3$) consist mainly of 3-sulfonatopropyl-1,1,1,3,5,5,5-heptamethyltrisiloxane, but they additionally contain small proportions of 3,5-bis(3-sulfonatopropyl)-1,1,1,3,5,7,7,7-octamethyltetrasiloxane. Their average composition corresponds to the formula

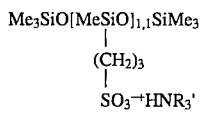

R'=H or Et

1% aqueous solutions of the compounds have a surface tension of $2.10^{-2}$ Nm$^{-1}$.

EXAMPLE 12

7.3 g of 3-chloropropyldimethoxymethylsilane (0.040 mol) are added dropwise at 100° C., over 1 hour, to a solution of 5 g of sodium sulfite in 30 ml of water, with vigorous stirring. The mixture is then refluxed for a further 45 minutes. The now almost clear solution is cooled to 80° C. and treated with 60 ml of ethanol and 0.5 g of potassium hydroxide. At the boiling point, 111.2 g of a mixture consisting of 110 g of dimethoxydimethylsilane (0.915 mol) and 1.2 g of trimethylmethoxysilane (0.012 mol) are then metered in over 3 hours, with intensive stirring. The resulting mixture is then cooled to room temperature, neutralized with 9 ml of 1N hydrochloric acid and evaporated under an oil-pump vacuum (20 Pa) at 60° C. The residue is dissolved in 200 ml of toluene, the solution is filtered and the filtrate is evaporated under the same conditions as above to give 72.1 g of a colorless pasty substance of average composition

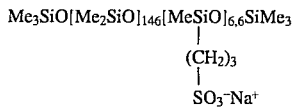

EXAMPLE 13

A mixture of 12 g of an α-hydroxy-ω-trimethylsilyldimethylpolysiloxane of average composition Me$_3$SiO[Me$_2$SiO]$_{15}$Me$_2$SiOH (9.4 mmol) and 1.3 g of triethylamine is treated at room temperature, over 20 minutes, with a solution of 1.7 g of pure 4,4-dimethyl-4-silabutane-1,4-sultone, prepared according to Example 1, in 70 ml of diethyl ether. The volatile constituents are then removed under an oil-pump vacuum (10 Pa) at 40° C. The residual light yellow oil (14.2 g) has the average composition

EXAMPLE 14

A solution of 20 g of poly(3-sulfonylpropylmethyl)siloxane, prepared according to Example 5, 230 g of a polydimethylsiloxane of the formula HO[SiMe$_2$O]$_{15}$H and 2.7 g of hexamethyldisiloxane in 200 ml of ethylene glycol dimethyl ether is stirred for 4 hours at 80° C. 9.45 g of [OSiMe(CH$_2$)$_3$NH(CH$_2$)$_2$NH$_2$]$_4$, dissolved in 35 ml of ethylene glycol dimethyl ether, are then metered in over 3 hours at this temperature. After removal of the solvent and other volatile constituents at 60° C. and 20 Pa, 246.2 g of a light yellow oil of average composition

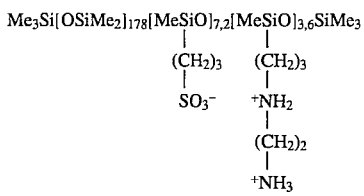

are obtained.

What is claimed is:

1. A process for the preparation of organosilicon compounds carrying sulfur-containing organic radicals, wherein organosilicon compounds made up of units of the general formula $$R_a(R^1O)_bR^2_cSiO_{(4-a-b-c)/2} \quad (I)$$

in which

R can be identical or different and is a monovalent organic radical,

R$^1$ can be identical or different and is a hydrogen atom or a monovalent organic radical, R$^2$ can be identical or different and is a radical —QX, where Q is a divalent aliphatic or cycloaliphatic hydrocarbon radical having 2 to 10 carbons atoms and X is a halogen atom, a is 0, 1, 2 or 3, b is 0, 1, 2 or 3 and c is 0, 1, 2 or 3, with the proviso that the organosilicon compound has at least one radical R$^2$ per molecule and the sum of a, b and c is less than or equal to 4, are reacted with sulfite in the presence of water.

2. A process according to claim 1, wherein the organosilicon compounds made up of units of formula (I) are silanes of the general formula $$R^6_d(R^7O)_eSiR^8_g \quad (II)$$

and/or partial hydrolyzates thereof, in which

R$^6$ can be identical or different and is a monovalent organic radical,

R$^7$ can be identical or different and is a hydrogen atom or a monovalent organic radical, R$^8$ can be identical or different and is a radical —QX, where Q is a divalent aliphatic or cycloaliphatic hydrocarbon radical having 2 to 10 carbon atoms and X is a halogen atom, d is 0, 1, 2 or 3, e is 0, 1, 2 or 3 and g is 1, 2 or 3, with the proviso that the sum d+e+g is equal to 4.

3. A process according to claim 1, wherein at least one silane of the general formula $$R^6_d(R^7O)_eSiR^8_g \quad (II)$$

and/or a partial hydrolyzate thereof, in which R$^6$, R$^7$, R$^8$, d, e and g are as defined in claim 2, with the proviso that the sum d+e+g is equal to 4 and e is an integer other than 0, and, optionally, a silane of the general formula $$R^4_fSi(OR^5)_{4-f} \quad (III)$$

and/or a partial hydrolyzate thereof, in which

R$^4$ can be identical or different and is a monovalent organic radical, $R^5$ can be identical or different and is a hydrogen atom or a monovalent organic radical, and f is 0, 1, 2 or 3, is reacted with sulfite in the presence of water.

4. A process according to claim 1, wherein the sulfite used is a compound which is soluble in water at 100° C. and 1013 hPa to the extent of at least 20 percent by weight, based on the total weight of the solution, said compound having the formula $$(M'_{v'})_2SO_3 \qquad (IV)$$

in which

M' can be identical or different and is a cation, with the exception of the proton, and v' has the reciprocal value of the charge of M'.

5. A process according to claim 1, wherein sulfite is used in amounts of 0.8 mol to 1.5 mol, based on one mol of radical X in the organosilicon compound made up of units of formula (I).

6. A process according to claim 1, wherein the reaction is carried out at a temperature of 20° C. to 220° C.

7. A process according to claim 1, wherein the reaction is carried out at a pressure of between 900 and 50,000 hPa.

8. A process according to claim 1, wherein the reaction is carried out in the presence of a catalyst.

9. A process according to claim 1, wherein the organosilicon compounds, carrying at least one radical bonded to silicon via carbon and having a sulfonate group or a grouping —$SO_2O$— bonded to form a ring, are equilibrated with at least one organosilicon compound (1).

10. A process according to claim 9, wherein the organosilicon compounds (1) used are those made up of units of the general formula $$R^9{}_i(R^{10}O)_hSiO_{(4-i-h)/2} \qquad (VI)$$

in which $R^9$ can be identical or different and is a hydrogen atom or a monovalent organic radical, $R^{10}$ can be identical or different and is a hydrogen atom or a monovalent organic radical, i is 0, 1, 2 or 3 and h is 0, 1, 2 or 3, with the proviso that the sum of i and h is less than or equal to 3.

* * * * *